(12) United States Patent
Huang et al.

(10) Patent No.: US 8,475,936 B2
(45) Date of Patent: Jul. 2, 2013

(54) ORGANIC COMPOUND AND ORGANIC ELECTROLUMINESCENCE DEVICE EMPLOYING THE SAME

(75) Inventors: Heh-Lung Huang, Taipei County (TW);
Chi-Jen Lin, Yunlin County (TW);
Teng-Chih Chao, Pingjhen (TW);
Hao-Chun Lee, Hsinchu (TW);
Chien-Hong Cheng, Hsinchu (TW)

(73) Assignee: Industrial Technology Research Institute, Hsinchu County (TW)

( * ) Notice: Subject to any disclaimer, the term of this patent is extended or adjusted under 35 U.S.C. 154(b) by 192 days.

(21) Appl. No.: 12/859,884

(22) Filed: Aug. 20, 2010

(65) Prior Publication Data

US 2011/0198571 A1     Aug. 18, 2011

(30) Foreign Application Priority Data

Feb. 12, 2010 (TW) ............................... 99104651 A

(51) Int. Cl.
*H01L 51/50* (2006.01)

(52) U.S. Cl.
USPC ........... 428/690; 428/917; 313/504; 313/505; 313/506; 257/40; 257/E51.05; 257/E51.026; 257/E51.032; 528/27; 528/394; 528/397; 528/442

(58) Field of Classification Search
USPC ..... 428/690, 917; 313/504, 505, 506; 528/27, 528/394, 397, 422; 257/40, E51.05, E51.026, 257/E51.032
See application file for complete search history.

(56) References Cited

U.S. PATENT DOCUMENTS

| | | | |
|---|---|---|---|
| 7,056,601 | B2 | 6/2006 | Cosimbescu et al. |
| 7,227,027 | B2 | 6/2007 | Qiu et al. |

(Continued)

FOREIGN PATENT DOCUMENTS

CN         1637114 A        7/2005

OTHER PUBLICATIONS

Baldo et al., Highly efficient phosphorescent emission from organic electroluminescent devices, 1998, Nature, vol. 395, pp. 151154.*

(Continued)

*Primary Examiner* — Jennifer Chriss
*Assistant Examiner* — Gregory Clark
(74) *Attorney, Agent, or Firm* — Pai Patent & Trademark Law Firm; Chao-Chang David Pai

(57) ABSTRACT

Organic compounds and organic electroluminescence devices employing the same are provided. The organic compound has a chemical structure represented as follows:

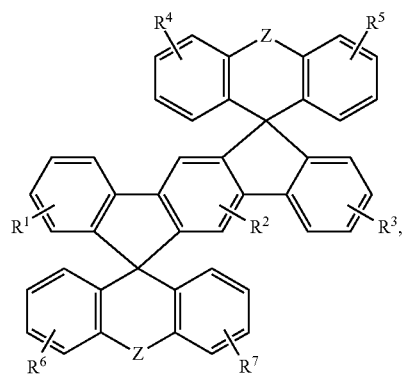

wherein: $R^1$, $R^2$, $R^3$, $R^4$, $R^5$, $R^6$, and $R^7$ are each independently an H, $C_{1-8}$ alkyl group, $C_{1-8}$ alkoxy group, $C_{1-8}$ halo-alkyl group, aryl group, heteroaryl group, cycloalkyl group, hetero-cycloalkyl group, or cycloaliphatic group; Z is independently

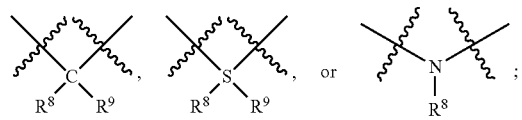

and $R^8$ and $R^9$ are each independent an aryl group, heteroaryl group, cycloalkyl group, hetero-cycloalkyl, or cycloaliphatic group.

14 Claims, 1 Drawing Sheet

U.S. PATENT DOCUMENTS

| | | |
|---|---|---|
| 7,252,893 B2 | 8/2007 | Ricks et al. |
| 2003/0205696 A1 | 11/2003 | Thoms et al. |
| 2004/0209115 A1 | 10/2004 | Thompson et al. |
| 2004/0209116 A1 | 10/2004 | Ren et al. |
| 2004/0247933 A1 | 12/2004 | Thoms |
| 2005/0123802 A1* | 6/2005 | Park et al. .................... 428/690 |
| 2006/0088728 A1 | 4/2006 | Kwong et al. |
| 2007/0141391 A1 | 6/2007 | Coggan et al. |
| 2007/0173657 A1 | 7/2007 | Chen et al. |

OTHER PUBLICATIONS

Kim et al., Synthesis of a Double Sprio-Polyindenofluorene with a Stable Blue Emission, 2005, Organic Letters, vol. 7, No. 19, pp. 4229-4232.*

First examination opinion notification issued by the China Intellectual Property Office on Jul. 4, 2012, (Application No. 201010143878.2).

* cited by examiner

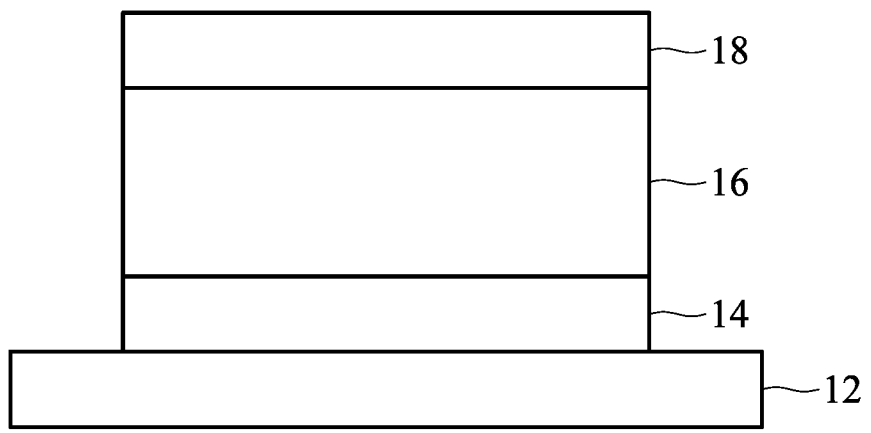

ORGANIC COMPOUND AND ORGANIC ELECTROLUMINESCENCE DEVICE EMPLOYING THE SAME

CROSS REFERENCE TO RELATED APPILCATIONS

This application is based upon and claims the benefit of priority from the prior Taiwan Patent Application No. 99104651, filed on Feb. 12, 2010, the entire contents of which are incorporated herein by reference.

BACKGROUND OF THE INVENTION

1. Field of the Invention

The invention relates to an organic compound and organic electroluminescence device employing the same and, more particularly, to an organic compound serving as a host material and a phosphorescent organic electroluminescence device employing the same.

2. Description of the Related Art

Recently, with the development and wide application of electronic products, such as mobile phones, PDAs, and notebook computers, there has been increasing demand for flat display elements which consume less electric power and occupy less space. Organic electroluminescent devices are self-emitting and highly luminous, with wide viewing angles, fast response speeds, and simple fabrication methods, making them an industry display of choice.

Generally, an organic electroluminescent device is composed of a light-emission layer sandwiched between a pair of electrodes. When an electric field is applied to the electrodes, the cathode injects electrons into the light-emission layer and the anode injects holes into the light-emission layer. When the electrons recombine with the holes in the light-emission layer, excitons are formed. Recombination of the electron and the hole results in light emission.

Depending on the spin states of the hole and electron, the exciton which results from the hole and electron recombination can have either a triplet or singlet spin state. Luminescence from a singlet exciton results in fluorescence light whereas luminescence from a triplet exciton results in phosphorescence light. The emissive efficiency of phosphorescence light is three times that of fluorescence light. Therefore, it is crucial to develop highly efficient phosphorescent material, in order to increase the emissive efficiency of the OLED.

In the application of organic electroluminescent devices, phosphorescent guest materials have to be used in combination with host materials which have a matching energy gap therewith, to achieve optimal electroluminescent performance and quantum yield. Particularly, since blue and green host materials require large energy gap differences between the host and guest material for electroluminescence, the host materials used in a phosphorescent OLED should have a short conjugated system. Further, in order to keep the key characteristics of the organic compound used in OLED (i.e. thermal-stability), the host material should also have a large molecular weight, which results in chemical structure design difficulties.

Certain organic compounds have been disclosed, using green or blue phosphorescent OLEDs, such as US Patent 2003/0205696A1 and US Patent 2007/0141391A1. Most of the disclosed organic compounds have moieties of carbazole or silyl benzene derivatives. However, the aforementioned compounds exhibit inferior thermal-stability or results in low current density of the OLED device.

Therefore, it is necessary to develop novel organic compounds suitable for phosphorescent OLEDs to solve the above problems.

BRIEF SUMMARY OF THE INVENTION

An exemplary embodiment of an organic compound has a Formula (I), of:

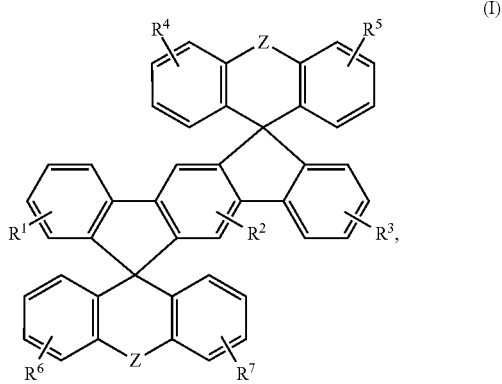

wherein: $R^1$, $R^2$, $R^3$, $R^4$, $R^5$, $R^6$, and $R^7$ are each independently an H, $C_{1-8}$ alkyl group, $C_{1-8}$ alkoxy group, $C_{1-8}$ haloalkyl group, aryl group, heteroaryl group, cycloalkyl group, hetero-cycloalkyl group, or cycloaliphatic group;

Z is independently

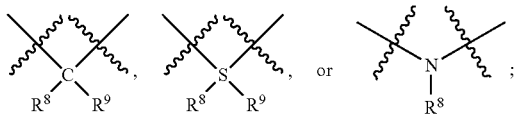

and $R^8$ and $R^9$ are each independent an aryl group, heteroaryl group, cycloalkyl group, hetero-cycloalkyl, or cycloaliphatic group.

In another exemplary embodiment of the invention, an organic electroluminescence device is provided. The device comprises a pair of electrodes and an electroluminescent element disposed between the pair of electrodes, wherein the electroluminescent element comprises the aforementioned organic compound.

Yet another exemplary embodiment of the invention provides an organic electroluminescence device comprising an emission layer which comprises a host material and a phosphorescent dopant. Particularly, the host material comprises the aforementioned organic compound and the emission layer emits blue or green light under a bias voltage.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein:

FIG. 1 shows a cross section of an organic electroluminescent device disclosed by an embodiment of the invention.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Organic Compound

The invention provides triarylaminec compounds with a spiro structure and an organic electroluminescence device comprising the same, wherein the triarylaminec compounds has a Formula (I), of:

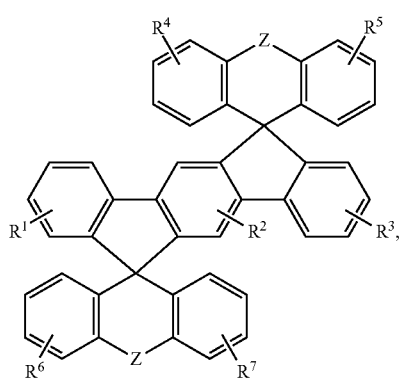

(I)

wherein $R^1$, $R^2$, $R^3$, $R^4$, $R^5$, $R^6$, and $R^7$ are each independently an H, $C_{1-8}$ alkyl group, $C_{1-8}$ alkoxy group, $C_{1-8}$ haloalkyl group, aryl group, heteroaryl group, cycloalkyl group, hetero-cycloalkyl group, or cycloaliphatic group, such as methyl group, ethyl group, propyl group, isopropyl group, butyl group, tert-butyl group, methoxy group, ethoxy group, propoxy group, isopropoxy group, butoxy group, isobutoxy group, phenyl group, biphenyl group, pyridyl group, furyl group, naphthyl group, anthryl group, phenanthrenyl group, imidazolyl group, pyrimidinyl group, quinolinyl group, indolyl group, or thiazolyl group.

and Z is independently

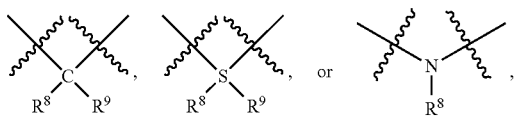

wherein $R^8$ and $R^9$ are each independent an aryl group, heteroaryl group, cycloalkyl group, hetero-cycloalkyl, or cycloaliphatic group. For example, $R^8$ and $R^9$ are each independently a substituted or unsubstituted phenyl group, biphenyl group, pyridyl group, furyl group, naphthyl group, anthryl group, phenanthrenyl group, imidazolyl group, pyrimidinyl group, quinolinyl group, indolyl group, or thiazolyl group.

The organic compounds of Formula (I) of the invention have high triplet energy ($^TEg$) gaps and are apt to transmit the energy to a guest emitter. Therefore, the organic compounds of Formula (I) of the invention are suitable for serving as host material of the blue or green phosphorescent organic electroluminescent devices; thereby increasing the efficiency thereof.

The organic compounds according to Formula (I) of the invention comprise the following compounds shown in Table 1. In addition, contractions thereof are also named and shown in Table 1.

TABLE 1

| Example | structure | contraction |
|---|---|---|
| 1 | 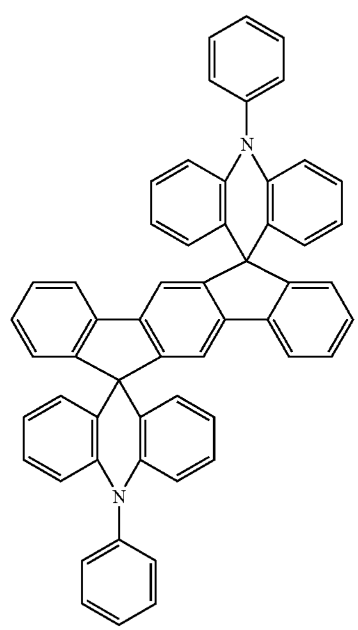 [SMILES: c1ccc(N2c3ccccc3C3(c4ccccc4-c4cc5c(cc43)-c3ccccc3C53c4ccccc4N(c4ccccc4)c4ccccc43)c3ccccc32)cc1] | Ds1 |

TABLE 1-continued
| Example | structure | contraction |
|---|---|---|
| 2 | 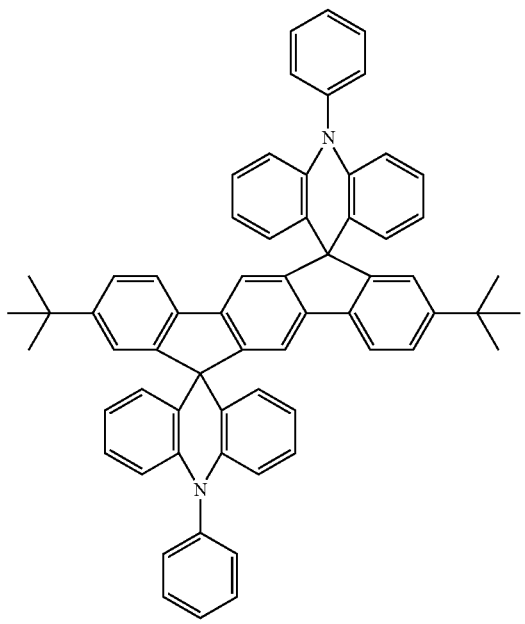 [SMILES: CC(C)(C)c1ccc2c(c1)C1(c3cc4c(cc3-2)C2(c3cc(C(C)(C)C)ccc3-4)c3ccccc3N(c3ccccc3)c3ccccc32)c2ccccc2N(c2ccccc2)c2ccccc21] | Ds2 |
| 3 | 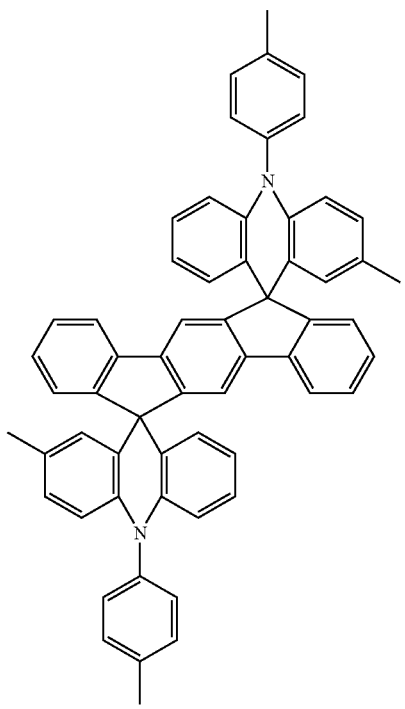 | Ds3 |

TABLE 1-continued

| Example | structure | contraction |
|---------|-----------|-------------|
| 4 | 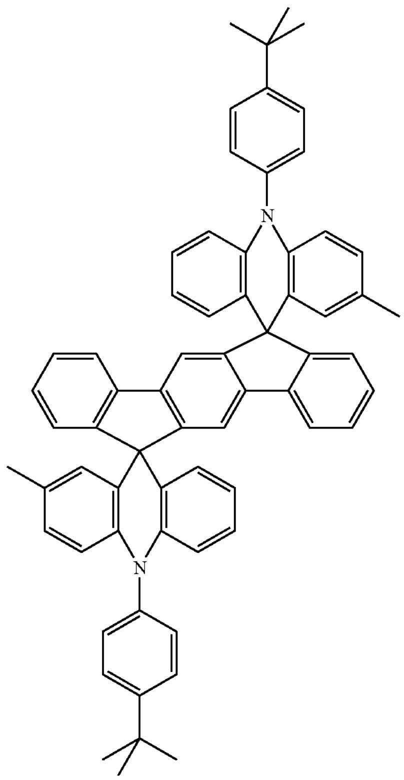 | Ds4 |

In order to clearly illustrate the method for preparing the organic compounds according to Formula (I), the preparation of compounds disclosed in Examples 1, 2, 3, and 4 are described in detail as below.

Example 1

Preparation of compound Ds1

First, 2,5-dibromo-p-xylene (2.64 g, 10 mmol), and KMnO₄ (10.0 g, 50 mmol) were add into a 500 ml bottle and dissolved into pyridine (20 ml) and water (10 ml), and the mixture was heated to reflux. 5 g of KMnO₄ (dissolved in 10 ml water) was added into the bottle at 30-minute intervals for four times. After refluxing overnight, the result was filtered through a celite. After concentration by vacuum distillation, an HCl aqueous solution (10%, 10 ml) was added into the filtrate. The result was extracted by ethyl acetate, and then the organic layer was dehydrated by magnesium sulfate, filtered and dried, obtaining a white solid as shown as compound (1) with a yield of 81%.

The synthesis pathway was as follows:

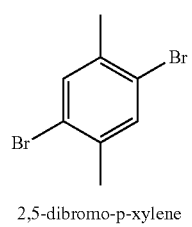

2,5-dibromo-p-xylene

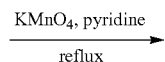
KMnO₄, pyridine
reflux

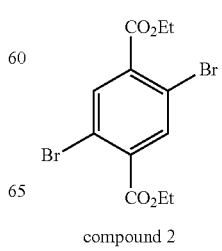

compound 1

Next, compound (3) (1.2 g, 5.8 mmol), compound (2) (1.0 g, 2.6 mmol), and Pd(PPh₃)₄ (182 mg, 0.16 mmol) were added into a bottle. Next, K₂CO₃ (2M in H₂O, 5.2 ml) and toluene (100 ml) were also added into the bottle, and then heated to reflux. After refluxing for 18 hrs, the result was extracted by methylene dichloride, and then the organic layer was washed by a saline solution, dehydrated by magnesium sulfate, filtered and dried. After purification by column chromatography with n-hexane/ethyl acetate (8:1) as the extraction solvent, a white solid as shown as compound (4) was obtained with a yield of 75%.

The synthesis pathway was as follows:

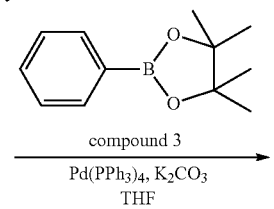

compound 2     compound 3
Pd(PPh₃)₄, K₂CO₃
THF

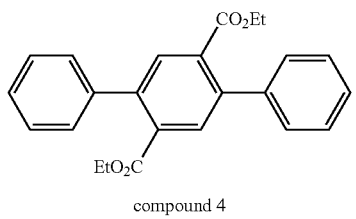

compound 4

Next, compound (4) (3.74 g, 10.0 mmol) and concentrated hydrochloric acid (30 ml) were added into a bottle, and heated to reflux. After refluxing for 3 hrs and then cooling to room temperature, the result was extracted by methylene dichloride, and then the organic layer was washed by a saline solution, dehydrated by magnesium sulfate, filtered and dried. After reprecipitation with methylene dichloride and n-hexane, a reddish solid as shown as compound (5) was obtained with a yield of 20%.

The synthesis pathway was as follows:

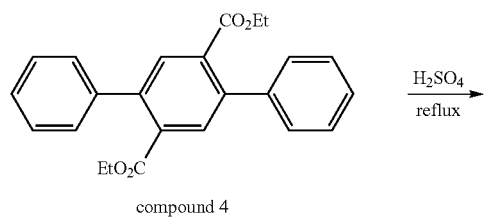

compound 4

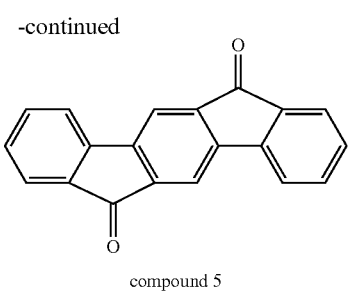

compound 5

Next, compound (6) (3.24 g, 10.0 mmol) was added into a bottle, and then filled and exhausted with nitrogen gas (three times). Next, tetrahydrofuran (20 ml) was added into the bottle and cooled down to −78° C. Next, n-BuLi (12.0 mmol, 0.77 g, 7.5 ml (1.6M in hexane)) was slowly added into the bottle. After stirring for 1 hr, compound (5) (5.0 mmole, 1.41 g) was added into the bottle at −78° C. After slowly warming to room temperature, the mixture was stirred to react at room temperature for 2 hrs.

Next, AcOH (30 ml) and HCl (3 ml) (as co-solvent) were added into the bottle and then heated to reflux for 3 hrs. After cooling to room temperature, the result was extracted by methylene dichloride, and then the organic layer was washed by a saline solution, dehydrated by magnesium sulfate, filtered and dried. After reprecipitation with methylene dichloride and n-hexane, a white solid as shown as compound Ds1 was obtained with a yield of 20%.

The synthesis pathway was as follows:

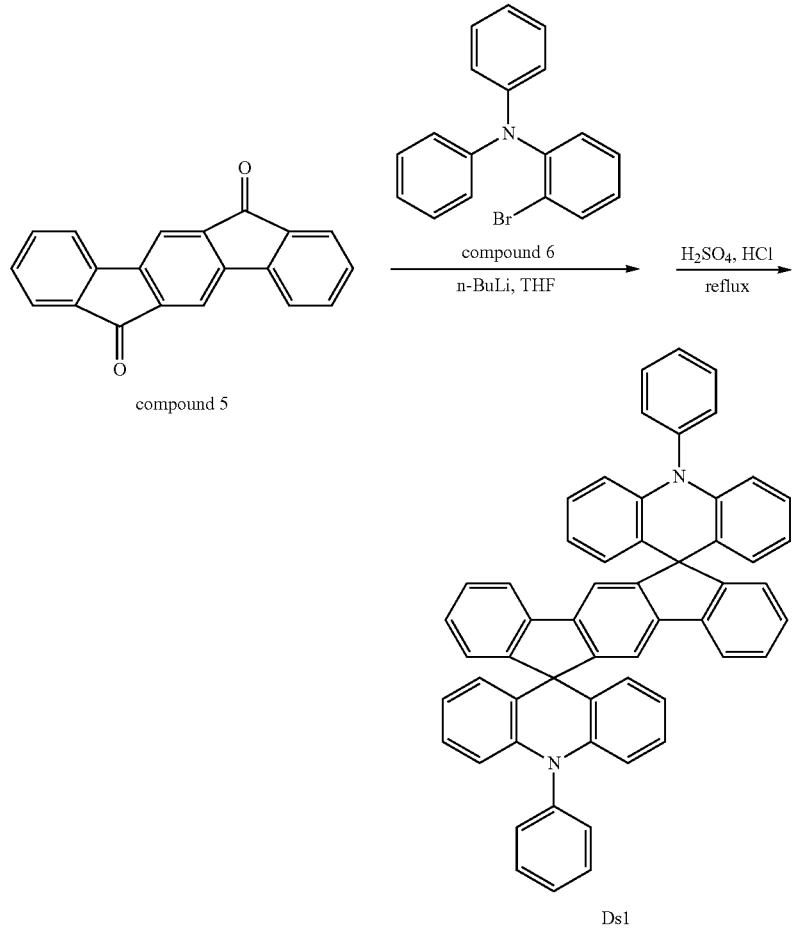

The $^1$H-NMR data of compound Ds1 was as shown below:
$^1$H NMR (CDCl$_3$, 400 MHz): δ 7.79 (d, J=7.6 Hz, 2H), 7.71 (t, J=7.6 Hz, 4H), 7.57 (t, J=7.6 Hz, 2H), 7.51 (m, 2H), 7.44 (d, J=7.6 Hz, 4H), 7.37 (t, J=7.6 Hz, 4H), 7.27 (s, 2H), 6.91 (td, J=8.4, 1.6 Hz, 4H), 6.56 (t, J=8.0 Hz, 4H), 6.41 (dd, J=7.6, 1.6 Hz, 4H), 6.35 (d, J=8.0 Hz, 4H).

Example 2

Preparation of Compound Ds2

Compound (7) (5.72 g, 22.0 mmol), compound (2) (3.80 g, 10.0 mmol), Pd(PPh$_3$)$_4$ (693 mg, 0.6 mmol), K$_2$CO$_3$ (2M in H$_2$O, 20 ml), and toluene (100 ml) were added into a bottle, and heated to reflux. After refluxing for 18 hrs, the result was extracted by ethyl acetate, and then the organic layer was dehydrated by magnesium sulfate, filtered and dried. After purification by column chromatography with n-hexane/ethyl acetate (8:1) as the extraction solvent, a white solid as shown as compound (8) was obtained with a yield of 72%.

The synthesis pathway was as follows:

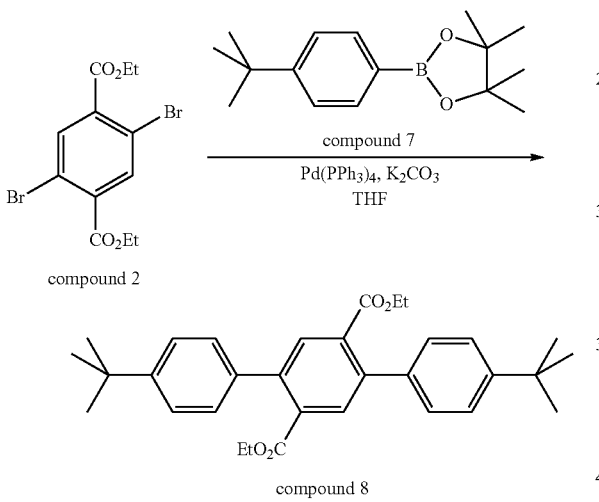

Next, compound (8) (4.87 g, 10.0 mmol) and concentrated hydrochloric acid (30 ml) were added into a bottle, and heated to reflux. After refluxing for 3 hrs and then cooling to room temperature, the result was extracted by methylene dichloride, and then the organic layer was washed by a saline solution, dehydrated by magnesium sulfate, filtered and dried. After reprecipitation with methylene dichloride and n-hexane, a reddish solid as shown as compound (9) was obtained with a yield of 18%.

The synthesis pathway was as follows:

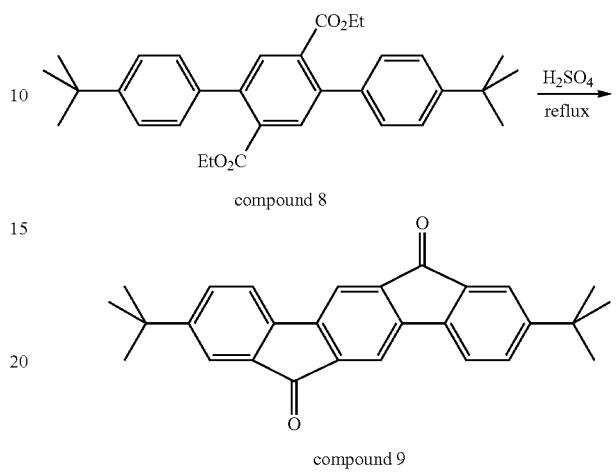

The $^1$H-NMR data of compound (9) was as shown below:
$^1$H NMR (CDCl$_3$, 200 MHz): δ 7.74 (s, 2H), 7.71 (s, 2H), 7.56 (dd, J=8.0, 1.8 Hz, 2H), 7.44 (dd, J=8.1, 1.8 Hz, 2H), 1.35 (s, 18H).

Next, compound (6) (3.24 g, 10.0 mmol) was added into a bottle, and then filled and exhausted with nitrogen gas (three times). Next, tetrahydrofuran (20 ml) was added into the bottle and cooled down to −78° C. Next, n-BuLi (12.0 mmol, 0.77 g, 7.5 ml 1.6M in hexane)) was slowly added into the bottle. After stirring for 1 hr, compound (9) (5.0 mmole, 1.97 g) was added into the bottle at −78° C. After slowly warming to room temperature, the mixture was stirred to react at room temperature for 2 hrs. Next, AcOH (30 ml) and HCl (3 ml) (as co-solvent) were added into the bottle and then heated to reflux for 3 hrs. After cooling to room temperature, the result was extracted by methylene dichloride, and then the organic layer was washed by a saline solution, dehydrated by magnesium sulfate, filtered and dried. After reprecipitation with methylene dichloride and n-hexane, a white solid as shown as compound Ds2 was obtained with a yield of 20%.

The synthesis pathway was as follows:

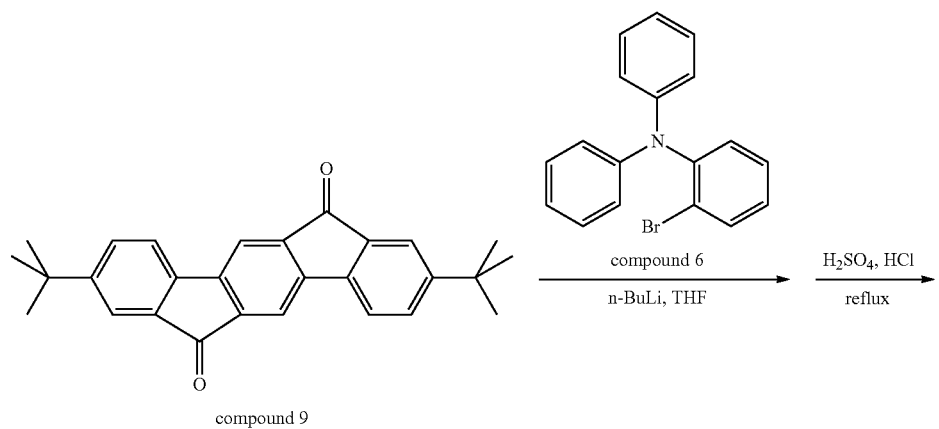

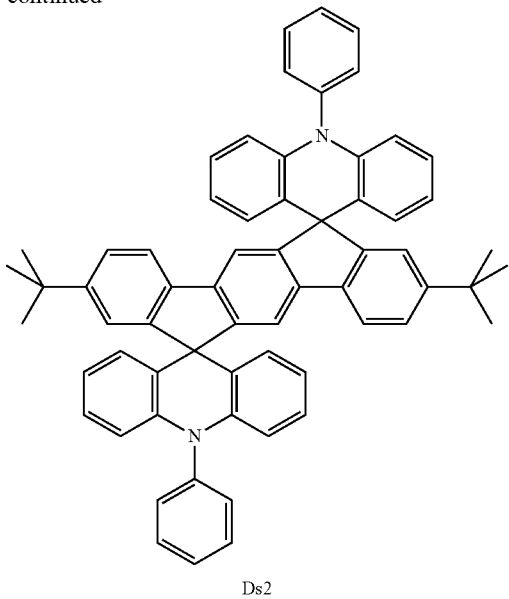

Ds2

The $^1$H-NMR data of compound Ds2 was as shown below:
$^1$H NMR (CDCl$_3$ 400 MHz): δ7.52 (t, J=8.4 Hz, 4H), 7.43 (td, J=8.4, 1.6 Hz, 2H), 7.28-7.21 (m, 8H), 7.09-6.99 (m, 12H), 6.91-6.84 (m, 8H), 1.37 (s, 18H).

The TG (glass transition temperature), HOMO (highest occupied molecular orbital) and LUMO (lowest unoccupied molecular orbital) energy gap, melting point, phosphorescent wavelength (measured at −78° C.), and $^T$Eg of compounds Ds1 and Ds2 were measured and are shown in Table 2.

TABLE 2

| Compound | LUMO (eV) | HOMO (eV) | Tg (° C.) | Tm (° C.) | Eg (eV) | $^T$Eg (eV) |
|---|---|---|---|---|---|---|
| Ds1 | 5.8 | 2.4 | — | 427 | 3.4 | 2.9 |
| DS2 | 5.7 | 2.4 | 167 | 430 | 3.3 | 2.9 |

Example 3

Preparation of Compound Ds3

Compound (11) (4.39 g, 12.5 mmol) was added into a bottle, and then filled and exhausted with nitrogen gas (three times). Next, tetrahydrofuran (20 ml) was added into the bottle and cooled down to −78° C. Next, n-BuLi (12.0 mmol, 0.77 g, 7.5 ml 1.6M in hexane)) was slowly added into the bottle. After stirring for 1 hr, compound (9) (5.0 mmole, 1.97 g) was added into the bottle at −78° C. and stirred overnight while warming to room temperature. Next, the result was extracted by ethyl acetate, and then the organic layer was dehydrated by magnesium sulfate, filtered and dried. Next, the result and acetic acid (100 ml) were added into a bottle and heated to 70° C. Next, hydrochloric acid was added into the bottle under 70° C. After stirring for 4 hrs, the result was extracted by ethyl acetate, and then the organic layer was dehydrated by magnesium sulfate, filtered and dried. After purification by column chromatography with n-hexane/ethyl acetate (20:1) as the extraction solvent, a canary yellow solid as shown as compound Ds3 was obtained. The synthesis pathway was as follows:

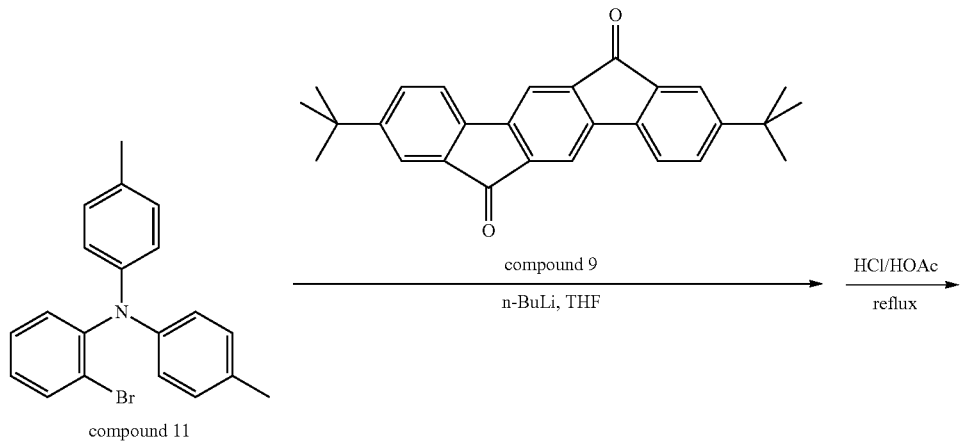

compound 11 compound 9
n-BuLi, THF

HCl/HOAc
reflux

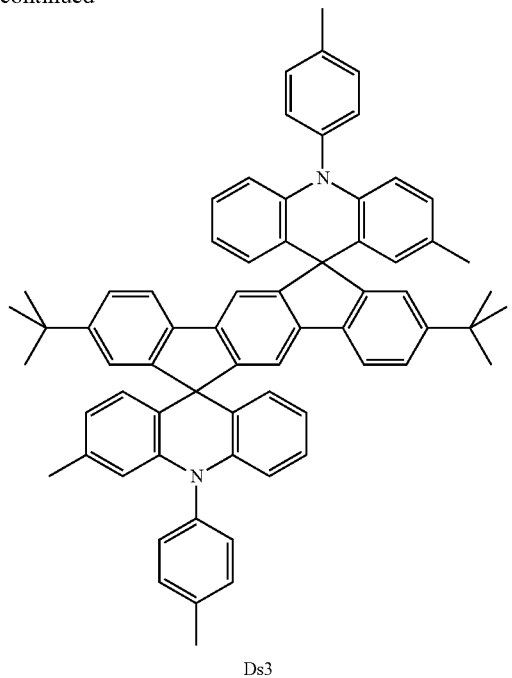

Ds3

The ¹H-NMR data of compound Ds4 was as shown below:
¹H NMR (CDCl₃, 400 MHz): δ 7.97 (d, J=1.0 Hz, 2H), 7.80 (d, J=1.2H, 2H), 7.74 (s, 4H), 7.58 (d, J=7.8 Hz, 2H), 7.44 (d, J=8.2 Hz, 2H), 7.18~7.38 (m, 24H), 2.40 (s, 3H), 2.33 (s, 3H), 1.38 (s, 18H).

Example 4

Preparation of Compound Ds4

Compound (12) (4.39 g, 12.5 mmol) was added into a bottle, and then filled and exhausted with nitrogen gas (three times). Next, tetrahydrofuran (20 ml) was added into the bottle and cooled down to −78° C. Next, n-BuLi (12.0 mmol, 0.77 g, 7.5 ml (1.6M in hexane)) was slowly added into the bottle. After stirring for 1 hr, compound (9) (5.0 mmole, 1.97 g) was added into the bottle at −78° C. and stirred overnight while warming to room temperature.

Next, the result was extracted by ethyl acetate, and then the organic layer was dehydrated by magnesium sulfate, filtered and dried. Next, the result and acetic acid (100 ml) were added into a bottle and heated to 70° C. Next, hydrochloric acid was added into the bottle under 70° C. After stirring for 4 hrs, the result was extracted by ethyl acetate, and then the organic layer was dehydrated by magnesium sulfate, filtered and dried. After purification by column chromatography with n-hexane/ethyl acetate (20:1) as the extraction solvent, a canary yellow solid as shown as compound Ds4 was obtained. Since the compound (12) can be reacted with the compound (9) via cyclization, alternatively, from the 4-methylbenzyl site or 4-tert-butylbenzyl site, two other side-products were also obtained except compound Ds4. The synthesis pathway was as follows:

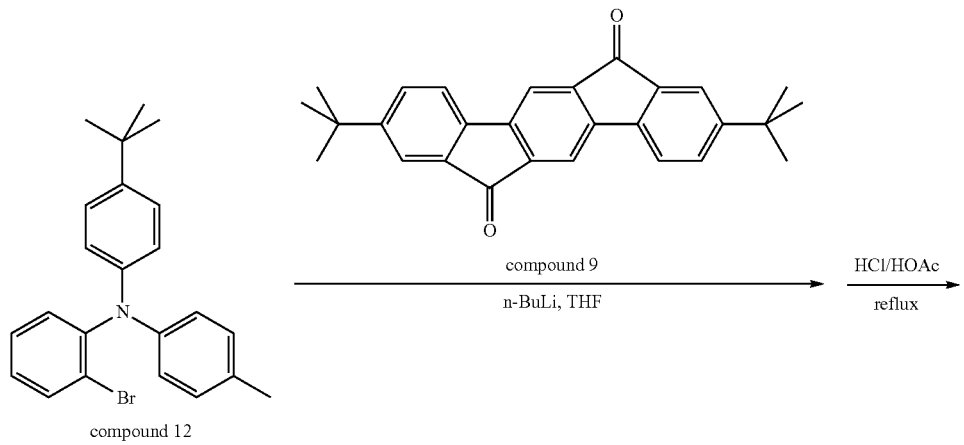

-continued

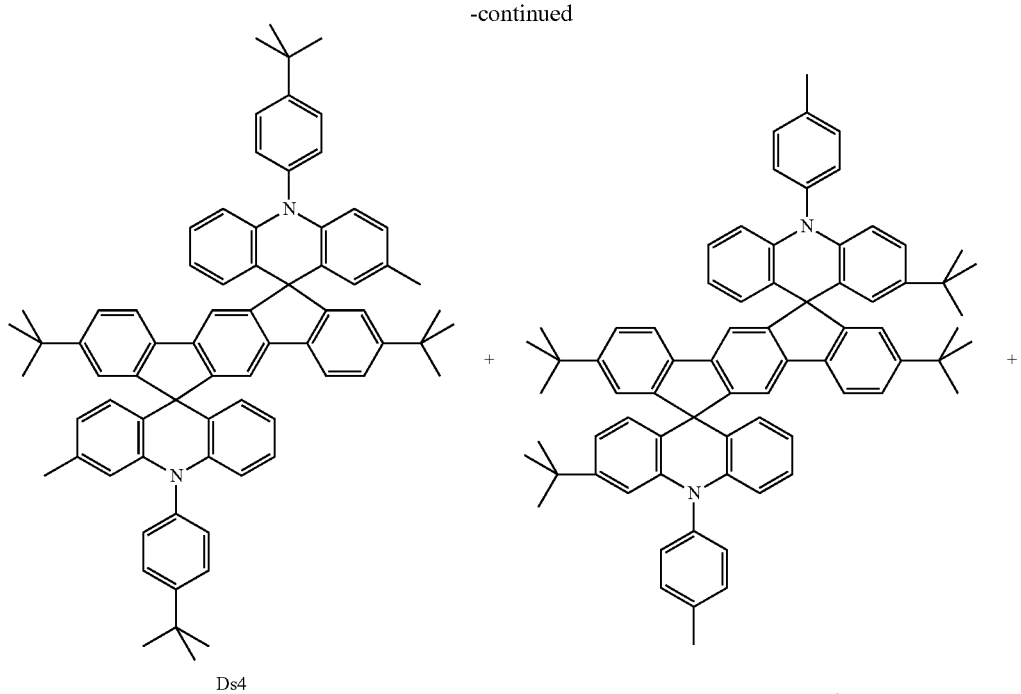

Ds4

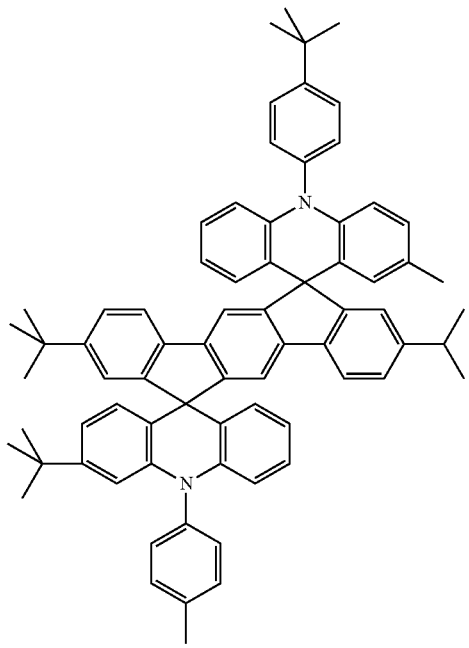

The $^1$H-NMR data of compound Ds4 was as shown below:
$^1$H NMR (CDCl$_3$, 400 MHz): δ 7.87~7.77 (m, 8H), 7.72~7.38 (m, 24H), 7.02~6.97 (m, 8H), 6.51~6.36 (m, 20H), 2.57 (s, 3H), 1.99 (s, 3H), 1.49 (s, 9H), 1.26 (s, 9H), 0.98 (s, 9H).

Organic Electroluminescence Device

FIG. 1 shows an embodiment of an organic electroluminescent device 10. The electroluminescent device 100 comprises a substrate 12, a bottom electrode 14, an electroluminescent element 16, and a top electrode 18, as shown in FIG. 1. The organic electroluminescent device can be top-emission, bottom-emission, or dual-emission devices.

The substrate 12 can be a glass plastic, or semiconductor substrate. Suitable material for the bottom and top electrodes can be Ca, Ag, Mg, Al, Li, In, Au, Ni, W, Pt, Cu, indium tin oxide (ITO), indium zinc oxide (IZO), aluminum zinc oxide (AZO), or zinc oxide (ZnO), formed by sputtering, electron beam evaporation, thermal evaporation, or chemical vapor deposition. Further, al least one of the bottom and top electrodes 14 and 18 is transparent.

The electroluminescent element 16 at least comprises an emission layer, and can further comprise a hole injection layer, a hole transport layer, an electron transport layer, and an electron injection layer. In embodiment of the invention, at least one layer of the electroluminescent element 16 comprises the aforementioned organic compound.

According to an embodiment of the invention, the organic electroluminescent device can be a phosphorescent organic electroluminescent device, and the phosphorescent organic electroluminescent device can comprise an emission layer comprising a host material and a phosphorescent dopant, wherein the host material comprises the aforementioned organic compounds.

In order to clearly disclose the organic electroluminescent devices of the invention, the following examples (using compound Ds2 as host materials and blue or green phosphorescent dopant) and comparative examples are intended to illustrate the invention more fully without limiting their scope, since numerous modifications and variations will be apparent to those skilled in this art.

Example 5

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, NPB (N,N'-di(naphthalene-1-yl)-N,N'-diphenyl-benzidine, with a thickness of 30 nm), Ds2 doped with Firpic (Iridium-bis(4,6difluorophenyl-pyridinato-$N,C^2$)-picolinate) (the ratio between Ds2 and Firpic was 100:6, with a thickness of 30 nm), BCP (2,9-dimethyl-4, 7diphenyl-1,10-phenanthroline, with a thickness of 15 nm), Alq3 (tris(8-hydroxyquinoline)aluminum, with a thickness of 30 nm), LiF (with a thickness of 1 nm), and Al (with a thickness of 100 nm) were subsequently formed on the ITO film at $10^{-5}$ Pa, obtaining the electroluminescent device (1). The emissive structure of the electroluminescent device (1) can be represented as:

ITO/NPB/D s2:FIrpic (6%)/BCP/Alq$_3$/LiF/Al.

The optical property of the electroluminescent device (1), as described in Example 5, was measured by a PR650 (purchased from Photo Research Inc.) and a Minolta TS110. The result is shown in Table 3.

Example 6

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, NPB (N,N'-di(naphthalene-1-yl)-N,N'-diphenyl-benzidine, with a thickness of 30 nm), mCP (N,N'-dicarbazolyl-3,5-dibenzene, with a thickness of 20 nm), Ds2 doped with Firpic (Iridium-bis(4,6difluorophenyl-pyridinato-$N,C^2$)-picolinate) (the ratio between Ds2 and Firpic was 100:6, with a thickness of 30 nm), BCP (2,9-dimethyl-4,7diphenyl-1,10-phenanthroline, with a thickness of 15 nm), Alq$_3$ (tris(8-hydroxyquinoline)aluminum, with a thickness of 30 nm), LiF (with a thickness of 1 nm), and Al (with a thickness of 100 nm) were subsequently formed on the ITO film at $10^{-5}$ Pa, obtaining the electroluminescent device (2). The emissive structure of the electroluminescent device (2) can be represented as:

ITO/NPB/mCP/Ds2:FIrpic(6%)/BCP/Alq$_3$/LiF/Al.

The optical property of the electroluminescent device (2), as described in Example 6, was measured by a PR650 (purchased from Photo Research Inc.) and a Minolta TS110. The result is shown in Table 3.

Example 7

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, TCTA (4,4',4''-tri(N-carbazolyl) triphenylamine, with a thickness of 30 nm), mCP (N,N'-dicarbazolyl-3,5-dibenzene, with a thickness of 20 nm), Ds2 doped with Firpic (Iridium-bis(4,6difluorophenyl-pyridinato-$N,C^2$)-picolinate) (the ratio between Ds2 and Firpic was 100:6, with a thickness of 30 nm), BCP (2,9-dimethyl-4, 7diphenyl-1,10-phenanthroline, with a thickness of 15 nm), Alq$_3$ (tris(8-hydroxyquinoline)aluminum, with a thickness of 30 nm), LiF (with a thickness of 1 nm), and Al (with a thickness of 100 nm) were subsequently formed on the ITO film at $10^{-5}$ Pa, obtaining the electroluminescent device (3). The emissive structure of the electroluminescent device (3) can be represented as:

ITO/TCTA/mCP/D s2:FIrpic (6%)/BCP/Alq$_3$/LiF/Al

The optical property of the electroluminescent device (3), as described in Example 7, was measured by a PR650 (purchased from Photo Research Inc.) and a Minolta TS110. The result is shown in Table 3.

Example 8

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, NPB (N,N'-di(naphthalene-1-yl)-N,N'-diphenyl-benzidine, with a thickness of 30 nm), mCP (N,N'-dicarbazolyl-3,5-dibenzene, with a thickness of 20 nm), Ds2 doped with Firpic (Iridium-bis(4,6difluorophenyl-pyridinato-$N,C^2$)-picolinate) (the ratio between Ds2 and Firpic was 100:6, with a thickness of 30 nm), TPBI (1,3,5-tris(phenyl-2-benzimidazolyl)-benzene, with a thickness of 20 nm), LiF (with a thickness of 1 nm), and Al (with a thickness of 100 nm) were subsequently formed on the ITO film at $10^{-5}$ Pa, obtaining the electroluminescent device (4). The emissive structure of the electroluminescent device (4) can be represented as:

ITO/NPB/mCP/Ds2:FIrpic (6%)/TPBI/LiF/Al

The optical property of the electroluminescent device (4), as described in Example 8, was measured by a PR650 (purchased from Photo Research Inc.) and a Minolta TS110. The result is shown in Table 3.

Comparative Example 1

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, TCTA (4,4',4''-tri(N-carbazolyl) triphenylamine, with a thickness of 30 nm), DAT (represented by a structure of

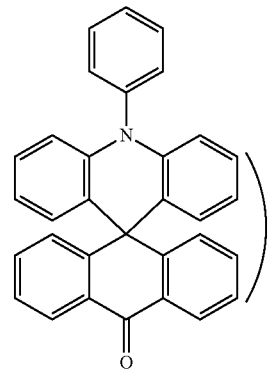 [SMILES: O=C1c2ccccc2C2(c3ccccc31)c1ccccc1N(c1ccccc1)c1ccccc12]

doped with Firpic (Iridium-bis(4,6difluorophenyl-pyridinato-N,C²)-picolinate) (the ratio between DAT and Firpic was 100:6, with a thickness of 30 nm), TPBI (1,3,5-tris(phenyl-2-benzimidazolyl)-benzene, with a thickness of 30 nm), LiF (with a thickness of 1 nm), and Al (with a thickness of 100 nm) were subsequently formed on the ITO film at 10⁻⁵ Pa, obtaining the electroluminescent device (5). The emissive structure of the electroluminescent device (5) can be represented as:

ITO/TCTA/DAT: Firpic(6%)/TPBI/LiF/Al

The optical property of the electroluminescent device (5), as described in Comparative Example 1, was measured by a PR650 (purchased from Photo Research Inc.) and a Minolta TS110. The result is shown in Table 3.

Comparative Example 2

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, TCTA (4,4',4''-tri(N-carbazolyl)triphenylamine, with a thickness of 30 nm), DAT (represented by a structure of

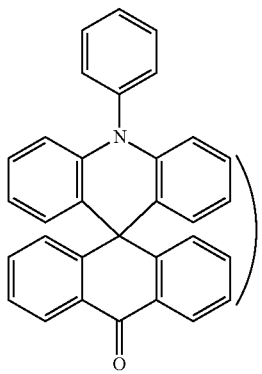 [SMILES: O=C1c2ccccc2C2(c3ccccc31)c1ccccc1N(c1ccccc1)c1ccccc12]

doped with Firpic (Iridium-bis(4,6difluorophenyl-pyridinato-N,C²)-picolinate) (the ratio between DAT and Firpic was 100:6, with a thickness of 30 nm), BCP (2,9-dimethyl-4,7diphenyl-1,10-phenanthroline, with a thickness of 30 nm), Alq₃ (tris(8-hydroxyquinoline)aluminum, with a thickness of 30 nm), LiF (with a thickness of 1 nm), and Al (with a thickness of 100 nm) were subsequently formed on the ITO film at 10⁻⁵ Pa, obtaining the electroluminescent device (6). The emissive structure of the electroluminescent device (6) can be represented as:

ITO/TCTA/DAT: FIrpic(6%)/BCP/Alq₃/LiF/Al

The optical property of the electroluminescent device (6), as described in Comparative Example 2, was measured by a PR650 (purchased from Photo Research Inc.) and a Minolta TS110. The result is shown in Table 3.

Comparative Example 3

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, TCTA (4,4',4''-tri(N-carbazolyl)triphenylamine, with a thickness of 30 nm), DAT (represented by a structure of

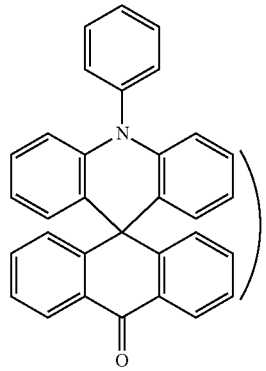 [SMILES: O=C1c2ccccc2C2(c3ccccc31)c1ccccc1N(c1ccccc1)c1ccccc12]

doped with Firpic (Iridium-bis(4,6difluorophenyl-pyridinato-N,C²)-picolinate) (the ratio between DAT and Firpic was 100:6, with a thickness of 30 nm), BPhen (4,7-diphenyl-1,10-phenanthroline, with a thickness of 30 nm), LiF (with a thickness of 1 nm), and Al (with a thickness of 100 nm) were subsequently formed on the ITO film at 10⁻⁵ Pa, obtaining the electroluminescent device (7). The emissive structure of the electroluminescent device (7) can be represented as:

ITO/TCTA/DAT: Flrpic(6%)/BPhen/LiF/Al

The optical property of the electroluminescent device (7), as described in Comparative Example 3, was measured by a PR650 (purchased from Photo Research Inc.) and a Minolta TS110. The result is shown in Table 3.

Comparative Example 4

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, TCTA (4,4',4''-tri(N-carbazolyl)triphenylamine, with a thickness of 30 nm), DAT (represented by a structure of

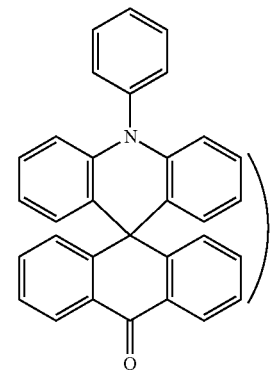 [SMILES: O=C1c2ccccc2C2(c3ccccc31)c1ccccc1N(c1ccccc1)c1ccccc12]

doped with Firpic (Iridium-bis(4,6difluorophenyl-pyridinato-N,C²)-picolinate) (the ratio between DAT and Firpic was 100:9, with a thickness of 30 nm), TPBI (1,3,5-tris(phenyl-2-benzimidazolyl)-benzene, with a thickness of 30 nm), LiF (with a thickness of 1 nm), and Al (with a thickness of 100 nm) were subsequently formed on the ITO film at 10⁻⁵ Pa, obtaining the electroluminescent device (8). The emissive structure of the electroluminescent device (8) can be represented as:

ITO/TCTA/DAT: Firpic (9%)/TPBI/LiF/Al

The optical property of the electroluminescent device (8), as described in Comparative Example 4, was measured by a PR650 (purchased from Photo Research Inc.) and a Minolta TS110. The result is shown in Table 3.

Comparative Example 5

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, TCTA (4,4',4''-tri(N-carbazolyl) triphenylamine, with a thickness of 30 nm), CBP (4,4'-N,N'-dicarbazole-biphenyl) doped with Firpic (Iridium-bis(4,6difluorophenyl-pyridinato-N,$C^2$)-picolinate) (the ratio between CBP and Firpic was 100:6, with a thickness of 30 nm), TPBI (1,3,5-tris(phenyl-2-benzimidazolyl)-benzene, with a thickness of 30 nm), LiF (with a thickness of 1 nm), and Al (with a thickness of 100 nm) were subsequently formed on the ITO film at $10^{-5}$ Pa, obtaining the electroluminescent device (9). The emissive structure of the electroluminescent device (9) can be represented as:

ITO/TCTA/CBP: FIrpic (6%)/TPBI/LiF/Al

The optical property of the electroluminescent device (9), as described in Comparative Example 5, was measured by a PR650 (purchased from Photo Research Inc.) and a Minolta TS110. The result is shown in Table 3.

thickness of 100 nm) were subsequently formed on the ITO film at $10^{-5}$ Pa, obtaining the electroluminescent device (10). The emissive structure of the electroluminescent device (10) can be represented as:

ITO/NPB/Ds2:Ir(ppy)$_3$(6%)/BCP/Alq$_3$/LiF/Al

The optical property of the electroluminescent device (10), as described in Example 9, was measured by a PR650 (purchased from Photo Research Inc.) and a Minolta TS110. The result is shown in Table 4.

Example 10

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, NPB (N,N'-di(naphthalene-1-yl)-N,N'-diphenyl-benzidine, with a thickness of 30 nm), Ds2 doped with Ir(ppy)$_3$ (the ratio between Ds2 and Ir(ppy)$_3$ was 100:6, with a thickness of 30 nm), TPBI (1,3,5-tris(phenyl-2-benzimidazolyl)-benzene, with a thickness of 30 nm), LiF (with a thickness of 1 nm), and Al (with a thickness of 100 nm) were subsequently formed on the ITO film at $10^{-5}$ Pa, obtaining the electroluminescent device (11). The emissive

TABLE 3

| No. | brightness (cd/m$^2$) | power efficiency (lm/W) | current efficiency (cd/A) | CIE |
|---|---|---|---|---|
| electroluminescent device (1) | 37000 (under 13.5 V) | 4.5 (under 5.0 V) | 17.2 (under 5.0 V) | (0.14, 0.31) |
| electroluminescent device (2) | 46000 (under 12.5 V) | 6.3 (under 5.5 V) | 21.9 (under 5.5 V) | (0.13, 0.28) |
| electroluminescent device (3) | 29000 (under 13 V) | 4.0 (under 4.5 V) | 13.8 (under 4.5 V) | (0.15, 0.33) |
| electroluminescent device (4) | 17000 (under 12.5 V) | 3.1 (under 6.0 V) | 10.8 (under 5.0 V) | (0.13, 0.29) |
| electroluminescent device (5) | 4644 (under 11 V) | 7.19 (under 4.0 V) | 9.16 (under 4.0 V) | (0.13, 0.30) |
| electroluminescent device (6) | 1733 (under 11 V) | 5.72 (under 6.5 V) | 2.57 (under 6.5 V) | (0.13, 0.29) |
| electroluminescent device (7) | 6668 (under 10.5 V) | 5.86 (under 4.5 V) | 8.39 (under 4.5 V | (0.13, 0.30) |
| electroluminescent device (8) | 2200 (under 11 V) | 10.2 (under 5.5 V) | 5.9 (under 5.5 V) | (0.12, 0.29) |
| electroluminescent device (9) | 1532 (under 13 V) | 3.27 (under 6.5 V) | 1.6 (under 6.5 V) | (0.26, 0.45) |

As shown in Table 3, with the premise that the same blue dopant was used, the organic compound Ds2 of the invention showed superior efficiency and brightness in comparison with the conventional organic host material CBP or DAT.

Example 9

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, NPB (N,N'-di(naphthalene-1-yl)-N,N'-diphenyl-benzidine, with a thickness of 30 nm), Ds2 doped with Ir(ppy)$_3$ (the ratio between Ds2 and Ir(ppy)$_3$ was 100:6, with a thickness of 30 nm), BCP (2,9-dimethyl-4,7diphenyl-1,10-phenanthroline, with a thickness of 10 nm), Alq3 (tris(8-hydroxyquinoline)aluminum, with a thickness of 40 nm), LiF (with a thickness of 1 nm), and Al (with a structure of the electroluminescent device (11) can be represented as:

ITO/NPB/D s2: Ir(ppy)$_3$(6%)/TPBI/LiF/Al

The optical property of the electroluminescent device (11), as described in Example 10 was measured by a PR650 (purchased from Photo Research Inc.) and a Minolta TS110. The result is shown in Table 4.

Comparative Example 6

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, TCTA (4,4',4''-tri(N-carbazolyl) triphenylamine, with a thickness of 30 nm), DAT (represented by a structure of

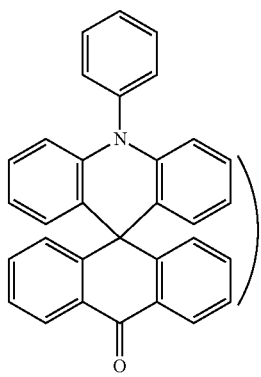 [SMILES: O=C1c2ccccc2C2(c3ccccc31)c1ccccc1N(c1ccccc1)c1ccccc12]

doped with Ir(ppy)₃ (the ratio between DAT and Ir(ppy)₃ was 100:6, with a thickness of 30 nm), TPBI (1,3,5-tris(phenyl-2-benzimidazolyl)-benzene, with a thickness of 30 nm), LiF (with a thickness of 1 nm), and Al (with a thickness of 100 nm) were subsequently formed on the ITO film at $10^{-5}$ Pa, obtaining the electroluminescent device (12). The emissive structure of the electroluminescent device (12) can be represented as:

ITO/TCTA/DAT:Ir(ppy)₃(6%)/TPBI/LiF/Al

The optical property of the electroluminescent device (12), as described in Comparative Example 6, was measured by a PR650 (purchased from Photo Research Inc.) and a Minolta TS110. The result is shown in Table 3.

Comparative Example 7

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, TCTA (4,4',4"-tri(N-carbazolyl) triphenylamine, with a thickness of 30 nm), DAT (represented by a structure of

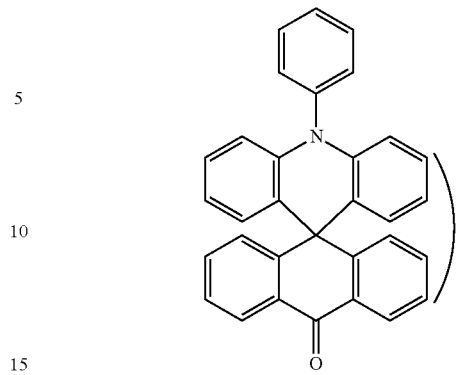

doped with Ir(ppy)₃ (the ratio between DAT and Ir(ppy)₃ was 100:9, with a thickness of 30 nm), BCP (2,9-dimethyl-4,7diphenyl-1,10-phenanthroline, with a thickness of 30 nm), Alq3 (tris(8-hydroxyquinoline)aluminum, with a thickness of 30 nm), LiF (with a thickness of 1 nm), and Al (with a thickness of 100 nm) were subsequently formed on the ITO film at $10^{-5}$ Pa, obtaining the electroluminescent device (13). The emissive structure of the electroluminescent device (13) can be represented as:

ITO/TCTA/DAT: Ir(ppy)₃ (9%)/BCP/Alq₃/LiF/Al

The optical property of the electroluminescent device (13), as described in Comparative Example 7, was measured by a PR650 (purchased from Photo Research Inc.) and a Minolta TS110. The result is shown in Table 3.

Comparative Example 8

A glass substrate with an indium tin oxide (ITO) film of 120 nm was provided and then washed with a cleaning agent, acetone, and isopropanol with ultrasonic agitation. After drying with a nitrogen flow, the ITO film was subjected to a UV/ozone treatment. Next, TCTA (4,4',4"-tri(N-carbazolyl) triphenylamine, with a thickness of 30 nm), CBP (4,4'-N,N'-dicarbazole-biphenyl) doped with Ir(ppy)₃ (the ratio between DAT and Ir(ppy)₃ was 100:6, with a thickness of 30 nm), BCP (2,9-dimethyl-4,7diphenyl-1,10-phenanthroline, with a thickness of 30 nm), Alq3 (tris(8-hydroxyquinoline)aluminum, with a thickness of 30 nm), LiF (with a thickness of 1 nm), and Al (with a thickness of 100 nm) were subsequently formed on the ITO film at $10^{-5}$ Pa, obtaining the electroluminescent device (14). The emissive structure of the electroluminescent device (14) can be represented as:

ITO/TCTA/CBP: Ir(ppy)₃ (6%)/BCP/Alq₃/LiF/Al

The optical property of the electroluminescent device (14), as described in Comparative Example 8, was measured by a PR650 (purchased from Photo Research Inc.) and a Minolta TS110. The result is shown in Table 4.

TABLE 4

| No. | brightness (cd/m²) | power efficiency (lm/W) | current efficiency (cd/A) | CIE |
| --- | --- | --- | --- | --- |
| electroluminescent device (10) | 110000 (under 15 V) | 15.7 (under 6 V) | 40.2 (under 5.5 V) | (0.25, 0.66) |
| electroluminescent device (11) | 67000 (under 15 V) | 10.7 (under 6 V) | 25.7 (under 5 V) | (0.25, 0.65) |
| electroluminescent device (12) | 12115 (under 11.5 V) | 4.2 (under 7.5 V) | 10.3 (under 8 V) | (0.37, 0.58) |
| electroluminescent device (13) | 32837 (under 10.5 V) | 5.02 (under 5.5 V) | 11.2 (under 7 V) | (0.27, 0.62) |
| electroluminescent device (14) | 15441 (under 11.5 V) | 12.5 (under 8 V) | 31.8 (under 8 V) | (0.33, 0.60) |

As shown in Table 4, with the premise that the same green dopant was used, the organic compound Ds2 of the invention showed superior efficiency and brightness in comparison with the conventional organic host material CBP or DAT.

While the invention has been described by way of example and in terms of embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organic compound having a Formula (I), of:

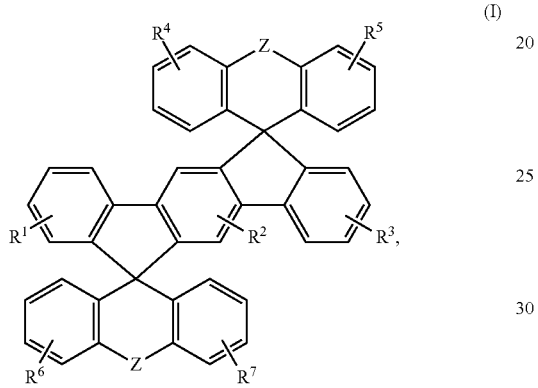

(I)

wherein: $R^1$, and $R^3$ are each independently H or $C_{1-8}$ alkyl group; and $R^2$, $R^4$, $R^5$, $R^6$, and $R^7$ are each independently an H, $C_{1-8}$ alkyl group, $C_{1-8}$ alkoxy group, $C_{1-8}$ halo-alkyl group, aryl group, heteroaryl group, cycloalkyl group, hetero-cycloalkyl group, or cycloaliphatic group; Z is independently

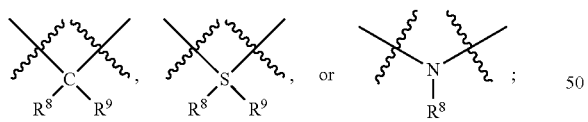

and $R^8$ and $R^9$ are each independent an aryl group, heteroaryl group, cycloalkyl group, hetero-cycloalkyl, or cycloaliphatic group.

2. The organic compound as claimed in claim 1, wherein $R^8$ and $R^9$ are each independently a substituted or unsubstituted phenyl group, biphenyl group, pyridyl group, furyl group, naphthyl group, anthryl group, phenanthrenyl group, imidazolyl group, pyrimidinyl group, quinolinyl group, indolyl group, or thiazolyl group.

3. The organic compound as claimed in claim 1, wherein the organic compound is

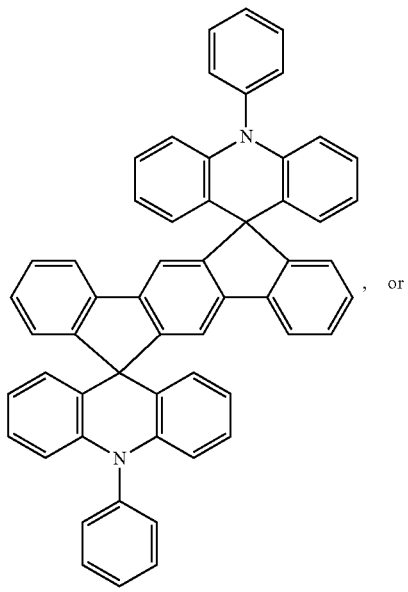

, or group, or cycloaliphatic group; Z is independently

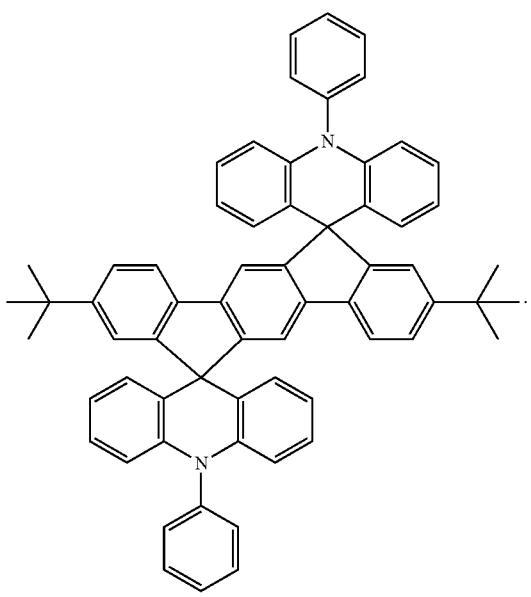

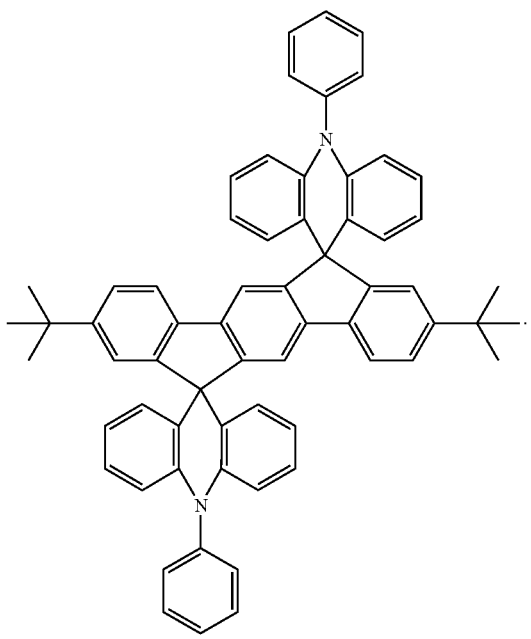

and R⁸ and R⁹ are each independent an aryl group, heteroaryl group, cycloalkyl group, hetero-cycloalkyl, or cycloaliphatic group.

4. An organic electroluminescence device, comprising:
a pair of electrodes; and
an electroluminescent element disposed between the pair of electrodes, wherein the electroluminescent element comprises the organic compound having a Formula (I), of:

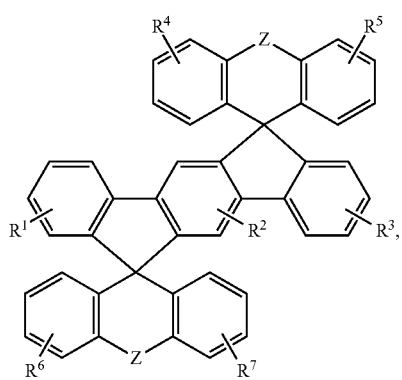

wherein: $R^1$, and $R^3$ are each independently H or $C_{1-8}$ alkyl group; and $R^2$, $R^4$, $R^5$, $R^6$, and $R^7$ are each independently an H, $C_{1-8}$ alkyl group, $C_{1-8}$ alkoxy group, $C_{1-8}$ halo-alkyl group, aryl group, heteroaryl group, cycloalkyl group, hetero-cycloalkyl wherein: $R^1$, and $R^3$ are each independently H or $C_{1-8}$ alkyl group; and $R^2$, $R^4$, $R^5$, $R^6$, and $R^7$ are each independently an H, $C_{1-8}$ alkyl group, $C_{1-8}$ alkoxy group, $C_{1-8}$ halo-alkyl group, aryl group, heteroaryl group, cycloalkyl group, hetero-cycloalkyl group, or cycloaliphatic group; Z is independently

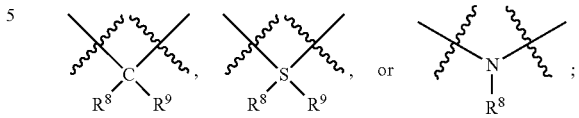

and R⁸ and R⁹ are each independent an aryl group, heteroaryl group, cycloalkyl group, hetero-cycloalkyl, or cycloaliphatic group.

5. The organic electroluminescence device as claimed in claim 4, wherein R⁸ and R⁹ are each independently a substituted or unsubstituted phenyl group, biphenyl group, pyridyl group, furyl group, naphthyl group, anthryl group, phenanthrenyl group, imidazolyl group, pyrimidinyl group, quinolinyl group, indolyl group, or thiazolyl group.

6. An organic electroluminescence device, comprising:
a pair of electrodes; and
an electroluminescent element disposed between the pair of electrodes, wherein the electroluminescent element comprises an emission layer comprising a host material and a phosphorescent dopant, and the host material comprises an organic compound having a Formula (I), of:

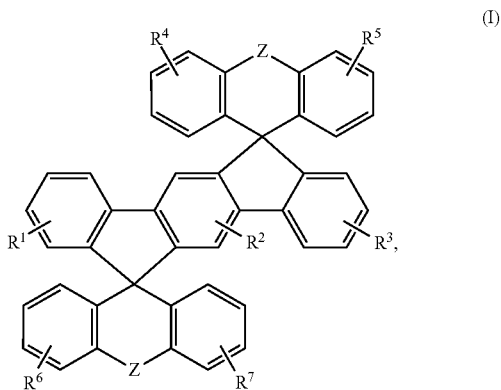

wherein: $R^1$, and $R^3$ are each independently H or $C_{1-8}$ alkyl group; and $R^5$, $R^6$, and $R^7$ are each independently an H, $C_{1-8}$ alkyl groups, $C_{1-8}$ alkosy gorup, $C_{1-8}$ halo-alkyl group, aryl gorup, heteroaryl group, cycloalkyl group, hetero-cycloalkyl group, or cycloaliphatic group; Z is independently

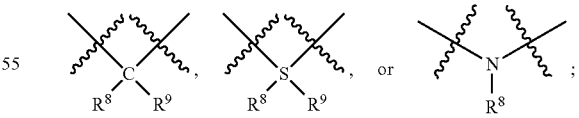

and R⁸ and R⁹ are each independent an aryl gorup, heteroaryl group, cyclalkyl group, hetero-cycloalkyl, or cycloaliphatic group.

7. The organic electroluminescence device as claimed in claim 6, wherein R⁸ and R⁹ are each independently a substituted or unsubstituted phenyl group, biphenyl group, pyridyl group, furyl group, naphthyl group, anthryl group, phenanthrenyl group, imidazolyl group, pyrimidinyl group, quinolinyl group, indolyl group, or thiazolyl group.

8. The organic electroluminescence device as claimed in claim 6, wherein the emission layer emits blue or green light under a bias voltage.

9. The organic compound as claimed in claim 1, wherein $R^2, R^4, R^5, R^6$, and $R^7$ are each independently a methyl group, ethyl group, propyl group, isopropyl group, butyl group, tert-butyl group, methoxy group, ethoxy group, propoxy group, isopropoxy group, butoxy group, isobutoxy group, phenyl group, biphenyl group, pyridyl group, furyl group, naphthyl group, anthryl group, phenanthrenyl group, imidazolyl group, pyrimidinyl group, quinolinyl group, indolyl group, or thiazolyl group.

10. The organic compound as claimed in claim 1, wherein $R^1$, and $R^3$ are each independently a methyl group, ethyl group, propyl group, isopropyl group, butyl group, or tert-butyl group.

11. The organic electroluminescence device as claimed in claim 4, wherein $R^2, R^4, R^5, R^6$, and $R^7$ are each independently a methyl group, ethyl group, propyl group, isopropyl group, butyl group, tert-butyl group, methoxy group, ethoxy group, propoxy group, isopropoxy group, butoxy group, isobutoxy group, phenyl group, biphenyl group, pyridyl group, furyl group, naphthyl group, anthryl group, phenanthrenyl group, imidazolyl group, pyrimidinyl group, quinolinyl group, indolyl group, or thiazolyl group.

12. The organic electroluminescence device as claimed in claim 4, wherein $R^1$, and $R^3$ are each independently a methyl group, ethyl group, propyl group, isopropyl group, butyl group, or tert-butyl group.

13. The organic electroluminescence device as claimed in claim 6, wherein $R^2$, $R^4$, $R^5$, $R^6$, and $R^7$ are each independently a methyl group, ethyl group, propyl group, isopropyl group, butyl group, tert-butyl group, methoxy group, ethoxy group, propoxy group, isopropoxy group, butoxy group, isobutoxy group, phenyl group, biphenyl group, pyridyl group, furyl group, naphthyl group, anthryl group, phenanthrenyl group, imidazolyl group, pyrimidinyl group, quinolinyl group, indolyl group, or thiazolyl group.

14. The organic electroluminescence device as claimed in claim 6, wherein $R^1$, and $R^3$ are each independently a methyl group, ethyl group, propyl group, isopropyl group, butyl group, or tert-butyl group.

* * * * *